United States Patent
Takebe

[11] Patent Number: 6,045,819
[45] Date of Patent: *Apr. 4, 2000

[54] SUBSTANCE CONTAINING HEALTH-PROMOTING COMPONENT AND PROCESS FOR THE PRODUCTION THEREOF

[75] Inventor: Minoru Takebe, Chiyoda-ku, Japan

[73] Assignee: Nichimo Co., Ltd., Tokyo, Japan

[*] Notice: This patent is subject to a terminal disclaimer.

[21] Appl. No.: 08/973,829

[22] PCT Filed: Apr. 10, 1997

[86] PCT No.: PCT/JP97/01253

§ 371 Date: Mar. 27, 1998

§ 102(e) Date: Mar. 27, 1998

[87] PCT Pub. No.: WO97/37549

PCT Pub. Date: Oct. 16, 1997

[30] Foreign Application Priority Data

Apr. 10, 1996 [JP] Japan .......................... 8-88552

[51] Int. Cl.$^7$ .............. A23L 1/20; A23K 1/00; A01N 65/00

[52] U.S. Cl. .............. 424/442; 426/46; 424/195.1; 424/400

[58] Field of Search .............. 424/195.1, 401, 424/442; 426/46

[56] References Cited

U.S. PATENT DOCUMENTS

| | | |
|---|---|---|
| 4,557,927 | 12/1985 | Miyake et al. . |
| 5,141,746 | 8/1992 | Fleury et al. . |
| 5,320,949 | 6/1994 | Shen . |
| 5,554,519 | 9/1996 | Weber et al. . |
| 5,679,806 | 10/1997 | Zheng et al. . |
| 5,789,581 | 8/1998 | Matsuura et al. . |
| 5,885,632 | 3/1999 | Takebe et al. . |

FOREIGN PATENT DOCUMENTS

| | | |
|---|---|---|
| 7-14927 | 2/1995 | Japan . |
| 7-289281 | 11/1995 | Japan . |
| 8-283283 | 10/1996 | Japan . |

*Primary Examiner*—Thurman K. Page
*Assistant Examiner*—Brian K. Seidleck
*Attorney, Agent, or Firm*—Koda & Androlia

[57] ABSTRACT

The process for preparing a product containing a healthful component according to the present invention is capable of providing a product containing a healthful component comprising at least one member of the group consisting of liver function improving constituents, cardiac function improving constituents, anti-inflammatory constituents antifat constituents, antioxidation constituents, and antimutagen constituents; and applied products containing the plain product as an ingredient, for example, foods which can be ingested in a large amount, livestock feeds and aquacultural feeds, cosmetics, diets of pets, and precursory products for pharmaceutical preparations. The process is capable of simply preparing the above-mentioned product in a large amount at a low cost. Heretofore, such products as the product of the present invention have not been provided at all. The present invention is characterized in that koji mold is inoculated on a pulse crop to effect koji preparation, and the resultant from the koji preparation is hydrolyzed to thereby obtain the product containing the healthful component having the above-mentioned excellent activities.

8 Claims, 3 Drawing Sheets

Fig. 1

SUBSTANCE CONTAINING HEALTH-PROMOTING COMPONENT AND PROCESS FOR THE PRODUCTION THEREOF

This application is a 371 of PCT/JP97/01253, filed on Apr. 10, 1997.

TECHNICAL FIELD

The present invention relates to a product containing a healthful or salutary component and a process for preparing the same. In particular, the product of the present invention is prepared from a pulse crop as a starting material. The term "pulse crop" used herein means leguminous crops such as soybean, defatted products and hycopotyls thereof, soy protein extracts, soy protein isolates and so forth, and the term "product" means products as such (plain products) which are made from a pulse crop as a starting material, applied products containing the plain product as an ingredient, for example, foods, livestock feeds and aquacultural feeds, cosmetics, diets of pets, and precursory products for pharmaceutical preparations.

BACKGROUND ART

In general, soybean which is one of the pulse crops contains isoflavone compounds including daidzin, daidzein, genistin and genistein.

The isoflavone compounds are represented by the following formula and Denotative Table.

Denotative Table

|  | R1 | R2 |
|---|---|---|
| daidzin | H | glucose |
| daidzein | H | H |
| genistin | OH | glucose |
| genistein | OH | H |

Of these isoflavone compounds, daidzein is an aglycone of daidzin having its glucose as a glycosidic saccharide hydrolytically separated therefrom, and genistein ia an aglycone of genistin having its glucose as a glycosidic saccharide hydrolytically separated therefrom. With respect to the isoflavone compounds, contents thereof and percentages between daidzin and daidzein and between genistin and genistein in a defatted soybean are shown in the following Table 1.

TABLE 1

|  | daidzin | daidzein | genistin | genistein |
|---|---|---|---|---|
| defatted soybean | 100 (96.9%) | 3.2 (3.1%) | 180 (97.7%) | 4.2 (2.3%) |

(unit: mg/100 g)

It is understood from Table 1 that, in soybean, daidzin and genistin are contained in large amounts while daidzein and genistein which are aglycones thereof are contained in smaller amounts.

On the other hand, it has been reported that a glycosidic saccharide is hydrolyzed from an isoflavone compound contained in soybean to form an aglycone in the course of soy sauce or miso (fermented soybean paste) preparation [see Kihara, K.: Journal of Japan Soy Sauce Research Institute (for SHO-KEN), 16, 5, 190(1990)].

According to this report, although hydrolysis of a glycosidic saccharide proceeds to some extent by cooking of a defatted soybean or in a koji preparation step (seigiku step), most of the saccharide has already hydrolytically been separated in soy sauce cake or a soybean miso. However, since these are highly salinized, it should be avoided to ingest these in large amounts. Accordingly, it is difficult to employ any of processes for preparing these as a process for preparing a food from a pulse crop as a starting material.

In soybeans soyasaponins occur. For example, in a defatted soybeans soyasaponins occur in an amount of 500 to 700 mg/100 g. It has been reported that soyasaponins consist of 5 varieties of saponins, i. e., soya saponin I, soya saponin II, soya saponin III, soya saponin A1 and soya saponin A2 in the form of a mixture [see Kitagawa et al.: YAKUGAKU ZASSHI, 104, 2, 162–168(1984)]. Each of these has glucuronic acid as a glycosidic saccharides and the aglycone which is such a compound that the glycosidic saccharide is removed therefrom includes two varieties of soyasapogenol A and soyasapogenol B. In general, however, the aglycone is present as soyasapogenol B. In a commercially available soybean miso, however, neither soyasapogenol A nor soyasapogenol B was detected.

Further, many reports have been made on pharmacological activities of various constituents contained in pulse crops.

For example, a *Pueraria lobata* OHWI (kudzu) which is one of legume has been used for a long time as a material for an infusion of Pueraria root (*Puerariae Radix*) as a herb medicine. It has been reported that isoflavone compounds and saponins contained in pueraria root have liver function improving activities (therapeutic activities against hepatopathy) [see "Nohara et al.: Journal of Medical and Pharmaceutical Society (for WAKAN-YAKU), 5, 408–409 (1988", "Y. Niiho etal.: YAKUGAKU ZASSHI, 109, 6, 424–431(1989)" and "Y. Niiho et al.: YAKUGAKU ZASSHI, 110, 8, 601–611(1990)"]. Specifically, an alcohol concentration, an acetaldehyde concentration and an con-centration of ketones in blood can be lowered to prevent hangover, nasty aftereffects of drink or the like, and metabolic dysfunction of liver can be prevented. Further, it has been reported that soyasaponins contained in soybean have anti-inflammatory activity, and activities of reducing serum cholesterol, neutral fat and phospholipid (cardiac function improving activity, lipotropic activity, antidiabetic activity, antifat activity, flesh reducing activity) as well as the above-mentioned activity in common with pueraria root [see Ohminami et al.: EIYO TO SHOKURYO, 34, 2, 105–108(1981)].

It is said that although soyasaponins have the activities of improving functions of a living body as described above, soyasaponins in the form of a glycoside as such can not be absorbed in a body. Accordingly, saponins in the form of a glycoside are not intestinally absorbable until it is decomposed into its aglycone, i.e., soyasapogenol B by enterobacteria having β-glucuronidase activity. It is said that the decomposition takes a lot of time and thus there the aglycone has a little chance of being absorbed by a small intestine to lead to an extremely low absorption efficiency. On the other hand, the enterobacteria having β-glucuronidase activity is not regarded as useful enterobacteria. Accordingly, placing no reliance on the decomposition by the enterobacteria, it is desired that soyasaponins be preliminarily decomposed in vitro into soyasapogenol B to ingest the latter. The same desire is true of the soy isoflavone compounds.

Further, soyasapogenol B is a triterpene compound and effective as an endotherine (ET) converter enzyme inhibitor (see Japanese Patent Laying-Open Publication No.188033/1995) and inhibits an endotherine converter enzyme from exhibiting its function, and hence soyasapogenol B is effective as a remedy for endotherine (ET)-related disorders such as hypertension, cerebrovascular contraction after subarachnoid hemorrhage, myocardial infarction, arteriosclerosis, heart failure, renal failure, asthma, and so forth. Further, the triterpene compound has lipase inhibitory activity and glycerophosphate dehydrogenase inhibitory activity. Accordingly, the triterpene compound is capable of inhibiting decomposition of lipids to prevent the lipids from being absorbed in a body, and thus, it is effective for prevention and treatment of fatness (see Japanese Patent Laying-Open Publication No.40689/1997, and Japanese Patent Laying-Open Publication No.67249/1997) and expected to exhibit cardial function improving activity and flesh reducing activity. Therefore, it is desired that soyasaponins be decomposed to obtain soyasapogenol B as an aglycone of saponins.

Moreover, it has been reported that free myo-inositol and the like which are formed by decomposition of phytic acid in contents of soybean have liver function improving activities of facilitating lipometabolism in a liver (therapeutic activities against hepatopathy) (see Kubota, H.: FOOD CHEMICAL, 8, 83–89 (1987).

Further description will be made on the promotion of liver function. It has been reported that miso soup has anti-cancer effect, and this is because enzyme activity of a liver is enhanced by ingestion of miso soup [see Kanke, S.: SHOKU NO KAGAKU, 224, 50–54(1996)]. Specifically, it is reported that when iron as a carcinogen and oxidant and miso are fed to a rat or mouse, activity of glutathione-s-transferase (GST) is increased. GST has been known to combine a carcinogen with glutathione to form a glutathione conjugate, which is excrete from a body. It is said that phase II xenobiotic-metabolizing enzymes to enhance carcinogen detoxication and elimination such as NAD(P)H: quinone oxidoreductase (DT diaphorase) and aldehyde dehydrogenase, as well as conjugating enzymes such as GST and UDP-glucuronosyl-transferase.

Accordingly, many proposals concerning isoflavone compounds contained in soybean have been made in Japanese Patent Laying-Open Publication No.126186/1987, Japanese Patent Laying-Open Publication No.258669/1989, Japanese Patent Laying-Open Publication No.170756/1993, and so on.

DISCLOSURE OF THE INVENTION

According to the method described in Japanese Patent Laying-Open Publication No.126186/1987, however, most of the resulting isoflavone compounds are daidzin and genistin which each has a glycosidic saccharides and aglycones are contained in the resultant in small amounts. Thus, it is impossible to obtain foods and the like which have excellent pharmacological effect as mentioned above.

The method described in Japanese Patent Laying-Open Publication No.258669/1989 is one which comprises hydrolytically separating a glycosidic saccharide from an isoflavone compound by action of β-glucosidase which is one of enzymes contained in soybean per se. However, aglycones are formed in a small proportion.

The method described in Japanese Patent Laying-Open Publication No.170756/1993 is one which comprises extractively separating isoflavone compounds from aglycones of the isoflavone compounds formed in soy sauce cake or soy sauce. Although the aglycones of the isoflavone compounds are formed in the course of soy sauce preparation in a very high proportion as described above, there is the following disadvantage. That is, the aglycones of the isoflavone compounds are present in soy sauce cake because of their insolubility, and soy sauce cake per se does not serve as a food. Accordingly, the method cannot be employed as a method for preparing a food. Further, aglycones of isoflavone compounds are also formed in a soybean miso at initial stage of preparation. However, a soybean miso has a problem that it should be avoided to ingest a soybean miso in a large amount because it is a highly salinized food.

With respect to a soybean miso (mame miso) a rice miso (kome miso), Daitokuji Soy nuggets (Daitokuji-natto: a Japanese fermented soyfood in the form of nuggets), dried-frozen tofu (Kori-dofu or Koya-dofu) (tofu: a Japanese food made of soymilk curds) and yuba (yuba: a Japanese food made of a film which forms on a surface of thick soymilk when the soymilk is gently heated) as commercially available foods made from a pulse crop as a starting materials contents of daidzin and daidzein and contents of genistin and genistein were comparatively measured. The results are as shown in the following Table 2.

TABLE 2

(unit: mg/100 g)

|  | daidzin | daidzein | genistin | genistein |
| --- | --- | --- | --- | --- |
| soybean miso | not detected | 78 | not detected | 57 |
| rice miso | 0.66 | 21 | 2.3 | 20 |
| Daitokuji-natto | not detected | 49 | not detected | 42 |
| dried-frozen tofu | 0.95 | 8.4 | 8.0 | 11 |
| yuba | 110 | 24 | 160 | 17 |

(detection limit: 0.5 mg/100 g)

It is understood from Table 2 that in the soybean miso, the rice miso and the Daitokuji-natto each of which has been subjected to fermentation treatment, daidzin and genistin have substantially been hydrolyzed, and in particular, the soybean miso and the Daitokuji-natto contain daidzein and genistein which are aglycones of daidzin and genistin in large amounts. However, a soybean miso and Daitokuji-natto should not be ingested in large amounts because of their high salt contents. It is also understood that in the dried-frozen tofu, each of daidzin, daidzein, genistin and genistein is contained in a small amount. It is further understood that similarly to the defatted soybean described above, the yuba contains daidzin and genistin in large amounts and daidzein and genistein which are aglycones thereof in small amounts.

Further, with respect to a soybean miso, a rice miso, Daitokuji Soy nuggets (Daitokuji-natto), dried-frozen tofu and yuba as commercially available foods made from pulse crops as starting materials, phytic acid contents were measured. The results are as shown in Table 3.

TABLE 3

(unit: mg/100 g)

| | phytic acid |
|---|---|
| soybean miso | not detected |
| rice miso | not detected |
| Daitokuji-natto | not detected |
| dried-frozen tofu | 506 |
| yuba | 361 |

(detection limit: 5 mg/100 g)

It is understood from Table 3 that in the soybean miso, the rice miso and the Daitokuji-natto each of which has been subjected to fermentation treatment, most of phytic acid has been hydrolyzed. However, a soybean miso and Daitokuji-natto should not be ingested in large amounts because of their high salt contents. It is further understood that each of the dried-frozen tofu and the yuba contains phytic acid in a large amount and thus, if ingested, no substantial myo-inositol is digested and absorbed.

Description will be made on further pharmacological activity. Of pulse crops, in particular, soybean has proteins as a main constituent, and a miso and a soy sauce are well-known as foods in which proteins of soybean are decomposed into peptides and amino acids by a protein hydrolyzing enzyme (protease) derived from koji mold. Further, it is said that in the miso and the soy sauce, proteins have been decomposed into low molecular forms to cause chemical reaction with carbohydrates or fats (Maillard reaction), consequently developing a brown color and aromatic smell (fragrant mellow smell). According to recent studies on the products resulting from Maillard reaction, it has been reported that intermediates resulting from Amadori rearrangement and final products, i.e., dark brown melanoidine or AGE (Advanced Glycation End Product) are formed, and these constituents are antimutagens [see Kato, H.: Miso Science and Technology, 41, 2, 40–48 (1993)]. However, the miso and the soy sauce have a problem that it should be avoided to ingest these in large amounts because these are highly salinized foods.

If foods containing a product containing a healthful component having excellent pharmacological activities as described above in a large amount can be ingested in a large amount, dietarily desired life is realized which exhibits excellent effect in terms of health maintenance of a human being. However, no foods have been provided which satisfy this demand.

In particular, the component potentially containing healthful component, which includes the isoflavone compounds, saponins, and phytic acid, has glycosidic saccharides as isoflavone compounds and saponins and forms chelate bonds as phytic acid, and is thus hardly absorbable by a gastrointestinal digestive tract of a human being or an animal. Accordingly, even if the component potentially containing healthful component is ingested in a large amount, it is impossible to improve liver function or the like.

Heretofore, it has been impossible to convert the isoflavone compounds, saponins, phytic acid and so on into forms readily digestible and absorbable.

The present invention has been made in view of these points. It is, therefore, an object of the present invention to provide a product containing a healthful component comprising at least one member of the group consisting of liver function improving constituents, cardiac function improving constituents, anti-inflammatory constituents, antifat constituents (flesh reducing constituents), antioxidation constituents, and antimutagen constituents; applied products containing the plain product as an ingredient, for example, foods which can be ingested in a large amount, livestock feeds and aquacultural feeds, cosmetics, diets of pets, and precursory products for pharmaceutical preparations; and a process for preparing a product containing a healthful component, which is capable of simply preparing the above-mentioned product in a large amount at a low cost.

To achieve the above object, the product containing a healthful component comprises a healthful component derived from inoculation of koji mold on a pulse crop to effect koji preparation and hydrolysis of the resultant from the koji preparation.

Further, the process according to the present invention for preparing a product containing a healthful component comprises: inoculating koji mold on a pulse crop to effect koji preparations and adding water to the resultant from the koji preparation to thereby hydrolyze the resultant, thereby forming the healthful component to prepare the product containing the healthful component.

Characteristically, the healthful component comprises at least one member of the group consisting of liver function improving constituents, cardiac function improving constituents, anti-inflammatory constituents, antifat constituents (flesh reducing constituents), antioxidation constituents, and antimutagen constituents; and further characteristically, the healthful component is so formed as to be absorbable by a digestive tract system.

According to the preparation process of the present invention, the healthful component can be formed in the product made from a pulse crop as a starting material by the koji preparation treatment and the hydrolysis treatment. Specifically, proteins, isoflavone compounds, saponins, phytic acid, etc. are converted into healthful constituents such as peptides, aglycones of the isoflavone compounds, aglycones of the saponins, myo-inositol, reaction products resulting from Maillard reaction, etc., which are absorbable by a digestive tract system of a human being or the like. According to the product of the present invention, promotion of health is extremely effectively realized by the at least one member of the group consisting of liver function improving constituents, cardiac function improving constituents, anti-inflammatory constituents, antifat constituents (flesh reducing constituents), antioxidation constituents, and antimutagen constituents. The product may be used as such or may be utilized as applied products containing the plain product as an ingredient, for example, foods, livestock feeds and aquacultural feeds, cosmetics, diets of pets, precursory products for pharmaceutical preparations, and so forth, thereby providing wide utilities. In addition, each of a miso and a soy sauce is highly salinized food because of addition of common salt subsequent to a koji preparation step and thus has not wide utilities, and yet, has a problem in productivity because of a very long ripening period subsequent to the koji preparation. In contrast thereto, the product of the present invention is prepared with ease at a low cost.

The product and the preparation process of the present invention are so designed as to function as described above. Accordingly, the healthful component can be formed in the product made from a pulse crop as a starting material by the koji preparation treatment and the hydrolysis treatment. Specifically, proteins, isoflavone compounds, saponins, phytic acid, etc. are converted into healthful constituents such as peptides, aglycones of the isoflavone compounds, aglycones of the saponins, myo-inositol, reaction products resulting from Maillard reaction, etc., which are absorbable by a digestive tract system of a human being or the like. According to the product of the present invention, promotion of health is extremely effectively realized by the at least one member of the group consisting of liver function improving constituents, cardiac function improving constituents, anti-inflammatory constituents, antifat constituents (flesh reducing constituents), antioxidation constituents, and antimutagen constituents. The product may be used as such. However, the aglycones of isoflavone compounds, aglycones of saponins, myo-inositol, Maillard reaction products, etc may be extracted and condensed to thereby promote efficacy. The product may be utilized as applied products made therefrom as a starting material or containing the same as an ingredient, for example, foods, livestock feeds and aquacultural feeds, cosmetics, diets of pets, precursory products for pharmaceutical preparations, and so forth. Accordingly, the product advantageously provide wide utilities. In addition, each of a miso and a soy sauce is highly salinized food because of addition of common salt subsequent to a koji preparation step and thus has not wide utilities, and yet, has a problem in productivity because of a very long ripening period subsequent to the koji preparation. In contrast thereto, the product of the present invention has an effect that it is prepared with ease at a low cost.

BEST MODE FOR CARRYING OUT THE INVENTION

Starting Material of Product

As a starting material of the product of the present inventions pulse crops may be used. In addition to pulse crops such as soybean, there may be used meal or cake thereof [for example, soybean meal (defatted soybean)], hypocotyl thereof, a soy protein extract (dried soy-milk powder), a soy protein isolate and the like.

Of these, hypocotyl, a soy protein extract and a soy protein isolate contain isoflavone compounds in large amounts and thus these are suitable as a starting material for preparation of a product containing aglycones of isoflavone compounds, in particular, genistein in high concentrations.

In this connection, of isoflavone compounds contained in soybean, contents of daidzin and daidzein and contents of genistin and genistein in soy proteins of a defatted soybean (soybean meal), a soy protein extract, soy protein isolate and a soy protein concentrate are as shown in the following Table 4.

TABLE 4

(unit: mg/100 g)

| | soy protein ext. | soy protein isolate | soy protein conc. |
|---|---|---|---|
| daidzin | 160 | 74 | 5.4 |
| daidzein | 2.5 | 8.9 | not detected |
| genistin | 250 | 170 | 8.7 |
| genistein | 2.3 | 16 | not detected |

(detection limit: 0.5 mg/100 g)

It is understood from Table 4 that in the soy proteins, contents of daidzin and genistin are high and contents of daidzein and genistein are low. Of four types of soy proteins shown in Table 4, the soy protein extract contains daidzin and genistin in amounts about 1.8 times and about 2.1 times as large as those of the defatted soybean, respectively, and the soy protein isolate contains genistin in an amount about 1.4 times as large as the defatted soybean. Accordingly, by utilizing these as a starting material, a product made from soy protein as a starting material may be prepared inexpensively with high production efficiency. In the soy protein extract and the soy protein isolate, due to preparation methods thereof which will be described below, water-soluble glycosidic isoflavone compounds are concentrated and contained in large amounts. By converting the glycosidic isoflavone compounds into aglycones by means of koji mold, isoflavone compounds containing aglycones in a large amount may inexpensively be prepared in a high yield. Further, if soybean itself from which the soy protein extract and the soy protein isolate are derived is produced from seeds so modified by gene manipulation as to be a variation containing isoflavone compounds in a large amount so that the soybean contains isoflavone compounds in a larger amount as compared with ordinary soybeans the soy protein extract and the soy protein isolate which are used as a starting material of the preparation method of the present invention contain isoflavone compounds in larger amounts. Accordingly, more aglycone-rich isoflavone compounds may inexpensively be formed in the product prepared by the present invention in a good yield.

If the thus prepared aglycone-rich isoflavone compounds are condensed to thereby obtain a material containing aglycones, in particular, genistein in high concentration, the material can be utilized as a material for a health food which contains genistein as a main component. Further, such a health food containing genistein in high concentration can be prepared with ease at a low cost.

In the following, embodiments of the present invention will be described with reference to the drawings.

Figure 1:
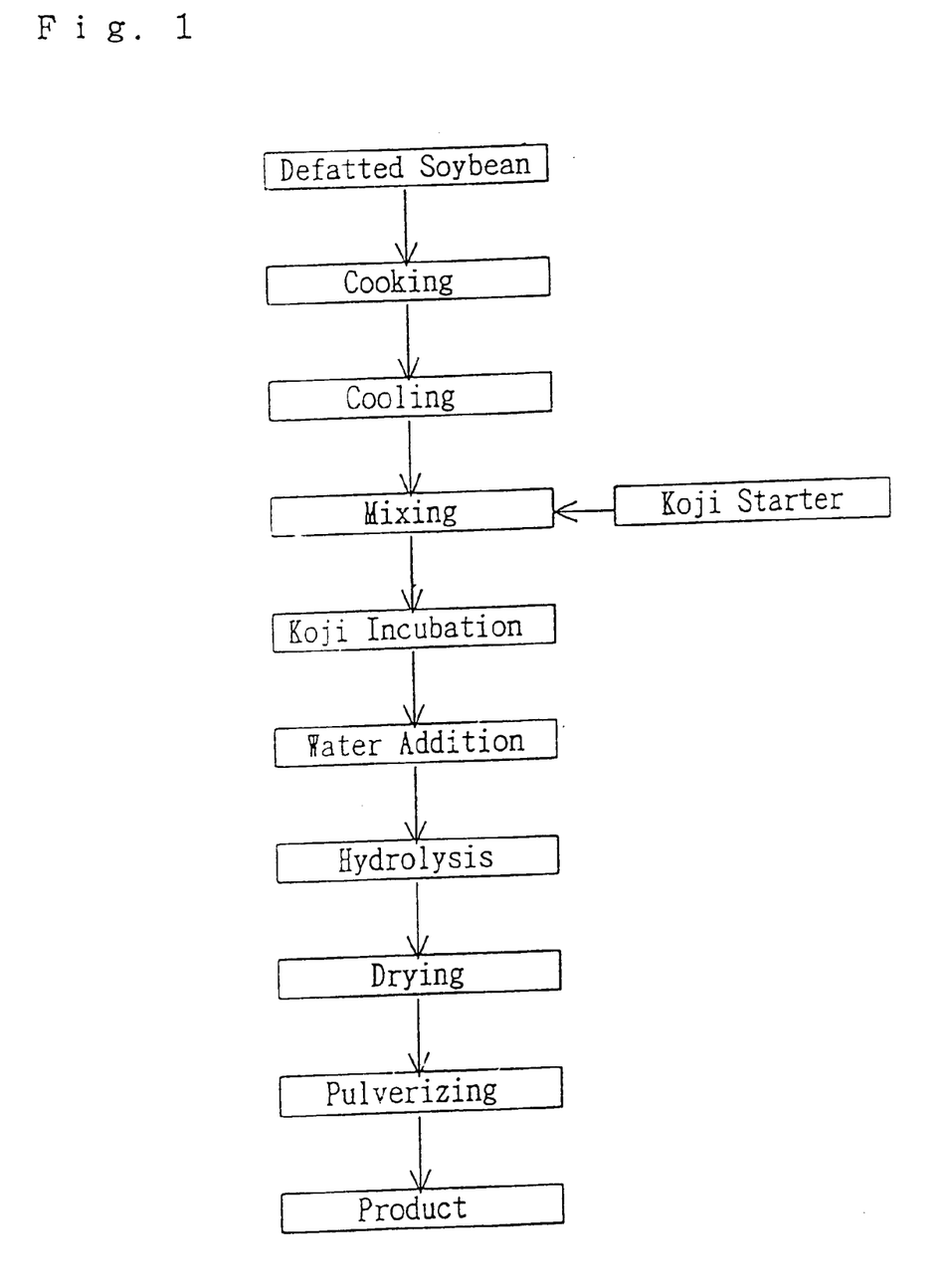
FIG. 1 is a flow chart showing one embodiment of the process for preparing the product according to the present invention which contains a healthful component.

FIG. 1 is a flow chart showing one embodiment of the process for preparing a product containing a healthful component derived from a potential healthful component contained in soybean which is one of pulse crops in accordance with the present invention.

Description will be given along the procedure in FIG. 1. First, a defatted soybean is cooked. By effecting the cooking, propagation of koji mold is promoted. The cooking of the defatted soybean may be conducted batchwise or continuously according to the purpose of preparation or the like.

After completion of the cooking, the defatted soybean is once cooled to adjust water content in the defatted soybean to a level allowing koji mold to propagate (for example, 40% by weight).

Incidentally, when a defatted soybean or the like is used as a starting material, the step of cooking may be omitted.

A soy protein extract is prepared by extracting a defatted soybean with water, performing centrifugation obtain an extract, and subjecting the extract to vacuum condensation, followed by spray drying. By the extraction with water, water-soluble glycosidic isoflavone compounds contained in the defatted soybean are extracted therefrom, and these are condensed and contained in the soy protein extract in a large amount. As such a soy protein extract, for example, there may be employed Solpee (trade name) which is commercially available one produced by Nisshin Oil Mills, Co., Ltd., and so forth. The soy protein extract is powdery. Accordingly, in order to effectively perform the subsequent koji preparation treatment according to the present invention, it is preferred that the soy protein extract be stirred while adding water thereto little by little to form granules of a few mm (about 1–2 mm) to about 10 mm in diameter. For example, it is preferred to add water to 200 g of the soy protein extract in an appropriate amount within a range of 70 to 200 ml. Further, the soy protein extract may be expansively molded by means of an extruder or the like to enable hyphae of koji mold to grow well. Alternatively, the powdery soy protein extract may be kneaded with water to form a block, and then the block is cut into slices or sticks.

On the other hand, a soy protein isolate is prepared by extracting a defatted soybean with water or a dilute alkali solution (0.02–0.1% sodium hydroxide solution), removing insoluble matter by centrifugation, adjusting pH with hydrochloric acid to a level of 4.2–4.5 to isoelectrically precipitate proteins, centrifuging the precipitate to obtain an isolate in the form of curds, washing the isolate with water, neutralizing the isolate with sodium hydroxide to dissolve, and heating and then spray-drying the resultant. By the extraction with water or a dilute alkali solution, water-soluble glycosidic isoflavone compounds contained in the defatted soybean are extracted therefrom, and these are condensed and contained in the soy protein isolate in a large amount. As the soy protein isolate, for example, there may be employed Fujipro E (trade name) which is commercially available one produced by Fuji-Purina Protein Co., Ltd., and so forth. In common with the soy protein extract, the soy protein isolate is also powdery. Accordingly, in order to effectively perform the subsequent koji preparation treatment according to the present invention, it is preferred that the soy protein extract be stirred while adding water thereto little by little to form granules of a few mm (about 1–2 mm) to about 10 mm in diameter. The amounts of the soy protein isolate and water may be substantially the same as in the soy protein extract.

When hypocotyls are used, the hypocotyls are subjected to substantially the same treatment as in the soy protein isolate to prepare for the subsequent koji preparation step.

The defatted soybean adjusted in the water content as described above is subjected to the process of the present invention as follows.

That is, the defatted soybean already cooked is inoculated with a koji starter comprising koji mold at a predetermined weight ratio, and mixing is conducted to uniformness.

Then, the mixture is placed into a device for preparing koji and kept in such a heated condition that the initial temperature is about 28 to 30° C. for a predetermined period of time to ferment the defatted soybean having a water content as low as 40% by weight with the koji mold, thereby effecting koji preparation until enzymes are formed which are necessary for converting proteins, glycosidic isoflavone compounds, soyasaponins, phytic acid, etc. contained in the defatted soybean into healthful (salutary) constituents such as peptides, aglycones of the glycosidic isoflavone compounds, aglycones of the soyasaponins, myo-inositol, reaction products resulting from Maillard reaction.

Specifically, with respect to the glycosidic isoflavone compounds and the soyasaponins, glycosidic saccharides thereof are hydrolytically separated to form the aglycones. With respect to the phytic acid which is such a compound that myo-inositol has its all hydroxyl groups each bonded with a phosphoric acid group, the phosphoric acid groups are liberated by a phytic acid hydrolyzing enzyme to form inositol pentaphosphate, inositol tetraphosphate, inositol triphosphate, inositol diphosphate, inositol monophosphate or inositol alone or a mixture thereof.

Of the formation of the healthful constituents, description will be given with respect to the formation of the aglycones of isoflavones and the aglycones of soyasaponins by hidrolytically separating glycosidic saccharides from isoflavones and saponins, respectively.

In these cases, the koji mold is propagated on and into the defatted soybean to thereby produce β-glucosidase which is an enzyme hydrolytically separating a glycosidic saccharide from an isoflavone compound, and by this enzyme, glycosidic saccharides are hydrolytically separated from the isoflavone compounds contained in the defatted soybean to form aglycones of the isoflavone compounds; and by β-glucruonidase which is an enzyme produced by the koji mold and hydrolytically separating a glycosidic saccharide from soyasaponins, glycosidic saccharides are hydrolytically separated from the soyasaponins contained in the defatted soybean to form aglycones of the soyasaponins.

As the koji mold used in the koji preparation, there may be employed those which are used in preparation of Japanese traditional fermented foods and tempeh and which are safely used for foods, for example, those classified as Aspergillus genus such as *Aspergillus usamii, Aspergillus kawachii, Aspergillus awamori, Aspergillus saitoi, Aspergillus oryzae* and *Aspergillus niger*; and those classified as Rhizopus genus.

The fermentation time depends upon the type of koji mold used. However, it is at least 24 hours and appropriately selected to be sufficient one for hydrolytically separating glycosidic saccharides from the isoflavone compounds and the soyasaponins in the defatted soybean to satisfactory extent.

Figure 2:
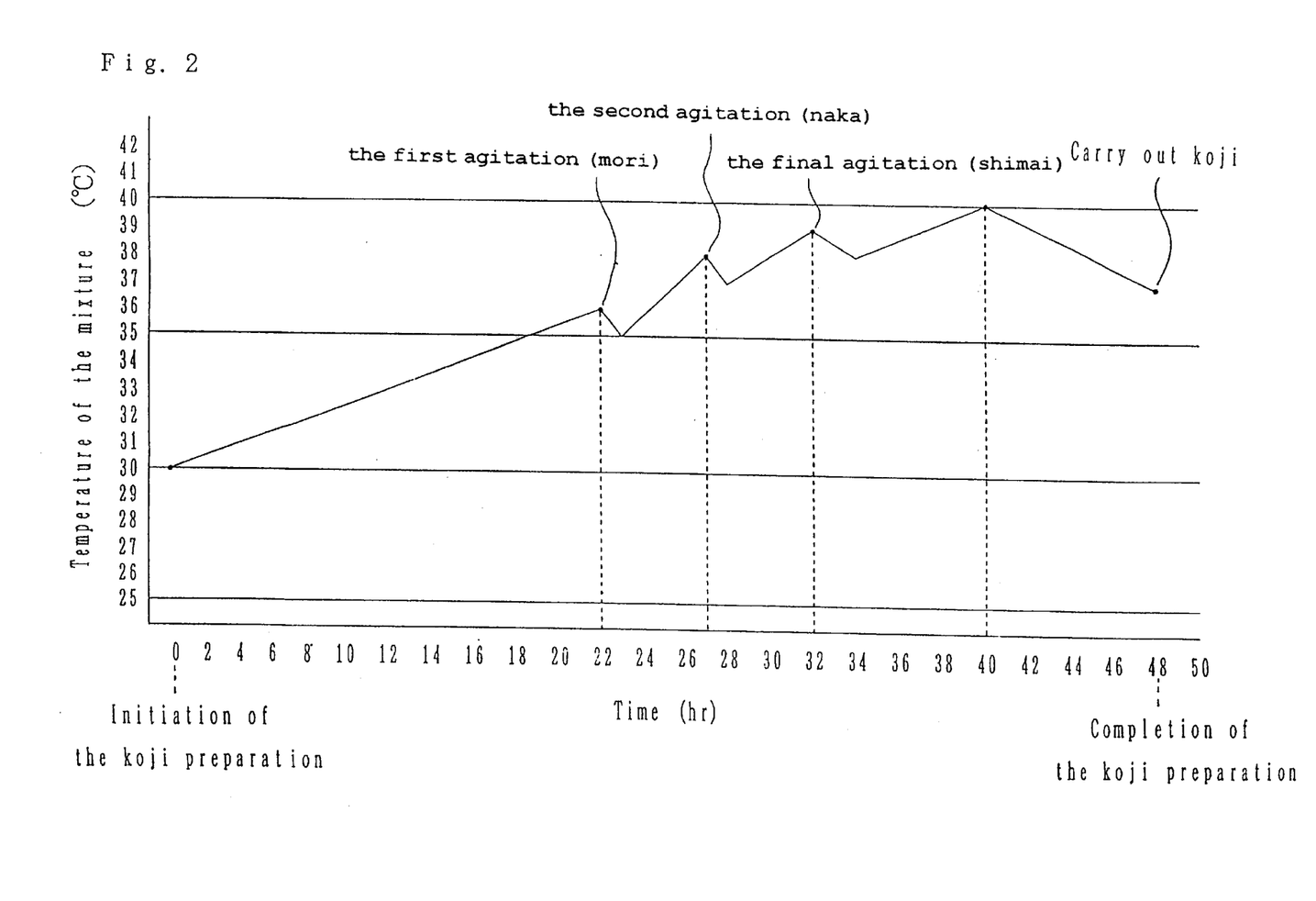
FIG. 2 is a diagram showing temperature characteristics of a mixture with progress of koji preparation time.

The temperature of the mixture in the device for preparing koji changes with times for example, as shown in FIG. 2, as koji preparation proceeds. That is, the temperature gradually rises until the state of the process of "the first agitation (mori)" is reached 22 hours after the initiation of the koji preparation, and the temperature slightly falls past "the first agitation (mori)". Then, the temperature rises again until the state of the process of "the second agitation (naka)" is reached 27 hours after the initiation of the koji preparation. Upon stirring the mixture at "the second agitation (naka)", the temperature slightly falls. Then, the temperature rises again until the stage of the process of "the final agitation (shimai)" is reached 32 hours after the initiation of the koji preparation. Upon stirring the mixture at "the final agitation (shimai)", the temperature slightly falls. Then, the temperature rises again up to 40 hours after the initiation of the koji preparation. Thereafter, the temperature gradually falls until the koji preparation reaches completion 48 hours after the initiation of the koji preparation.

Then, water is added to the product resulting from the koji preparation, and the mixture is kept in a heated condition at 30 to 65° C. for a predetermined period of time to hydrolyze proteins while sufficiently separating glycosidic saccharides from the isoflavone compounds and the saponins which are contained in the defatted soybean by the hydrolytic action of β-glucosidase and β-glucuronidase which are contained in the resulting product to form aglycones of the isoflavone compounds and the saponins.

With respect to the hydrolysis of the proteins, hydrolysis time and hydrolysis temperature are appropriately selected depending upon the type of koji mold used so that the glycosidic saccharides are separated from the isoflavone compounds and the saponins in the defatted soybean to satisfactory extent.

In this manner, organic acids are formed in the initial stage of the fermentation to inhibit contaminants in the defatted soybean from propagating, thereby eliminating undesired possibility of secondary contamination. Consequently, a product made from a defatted soybean as a starting material can be mass-produced.

Table 5 shows contents of isoflavone compounds in 100 g of a defatted soybean which is prepared by subjecting an untreated defatted soybean to koji preparation initiated at an initial temperature of 30° C. and completed over a period of 48 hours, adding water to the resulting product in the same weight as that of the resulting product, and subjecting the mixture to hydrolysis of proteins at 30° C. for 24 hours.

TABLE 5

| daidzin | daidzein | genistin | genistein |
|---------|----------|----------|-----------|
| 25 | 74 | 53 | 59 |

(unit: mg/100 g)

According to Table 5, daidzein and genistein which are aglycones of isoflavone compounds are contained in greatly increased amounts of 74 mg and 59 mg which are about 23 times and 14 times as large as the amounts in the conventional example shown in Table 1, respectively. From this, it is understood that daidzein and genistein can be formed in further increased amounts by effecting the hydrolysis of proteins for 24 hours or more after the completion of the koji preparation.

In another example, the treatment according to the process of the present invention was applied to an untreated defatted soybean and a soy protein isolate, and Table 6 comparatively shows, for the same purpose as that of Table 5, measurements thereon prior and posterior to the treatment.

Explanation is first made with respect to one of them, i.e., the defatted soybean. Proportions of starting materials and koji mold was such that 100 g of a defatted soybean, 0.1 g of a roughly polished rice, and 8×10$^7$ koji spores/g were used. With such proportions, the untreated defatted soybean was subjected to koji preparation initiated at an initial temperature of 30° C. and completed over a period of 48 hours, and water was added to the resulting product in the same weight as that of the resulting product, and the mixture was subjected to hydrolysis of proteins at 50° C. for 48 hours. The results are as shown in Table 6.

As the other of them, i.e., the commercially available soy protein isolate, Fujinic 200 (trade name) manufactured by Fuji-Purina Protein Co., Ltd. was used. Proportions of starting materials and koji mold was such that 100 g of a defatted soybean, 0.1 g of a roughly polished rice, and 8×10$^7$ koji spores/g were used. With such proportions, the untreated commercially available soy protein was subjected to koji preparation initiated at an initial temperature of 30° C. and completed over a period of 48 hours, and water was added to the resulting product in the same weight as that of the resulting product, and the mixture was subjected to hydrolysis of proteins at 50° C. for 48 hours. The results are as shown in Table 6.

TABLE 6

|  | defatted soybean | | coml. soy protein | |
|--|------|------|------|------|
|  | pre | post | pre | post |
| daidzin | 100 | not detected | 90 | 1.0 |
| daidzein | 3.2 | 70 | 5.3 | 100 |
| genistin | 120 | 1.3 | 120 | 3.3 |
| genistein | 4.2 | 64 | 4.4 | 94 |

(unit: mg/100 g)

According to Table 6, in the defatted soybean, daidzein and genistein which are aglycones of isoflavone compounds are contained in greatly increased post-treatment amounts of 70 mg and 64 mg which are about 22 times and 15 times as large as the pre-treatment values, respectively. In addition, daidzin which is an isoflavone compound having a glycosidic saccharide is decomposed to an undetectable extent, and the amount of genistin is extremely reduced to a level as low as 1.3 mg.

Likewise, in the commercially available soy protein, daidzein and genistein which are aglycones of isoflavone compounds are contained in greatly increased post-treatment amounts of 100 g and 94 mg which are about 19 times and 21 times as large as the pre-treatment values, respectively. In addition, the amounts of daidzin and genistin which are isoflavone compounds each having a glycosidic saccharide are extremely reduced to levels as low as 1.0 mg and 1.3 mg, respectively.

As described above, according to the present invention, with respect to the isoflavone compounds and the saponins and the like which are contained in soybean, aglycones thereof that have high pharmacological activities can be prepared at extremely high formation ratios.

Table 7 shows contents of isoflavone compounds in a soy protein extract as Embodiment A in which water was added to 200 g of a soy protein extract in an appropriate amount within a range of 70 to 200 ml and stirring was conducted, and a blend of 50 g of the soy protein extract in the form of a powder and 0.3 g of koji mold (*Aspergillus niger*) was mixed therein, and the thus prepared material was subjected to koji preparation at 30° C. over a period of 48 hours, and water was added to the resulting product in the same weight as that of the resulting product, and the mixture was subjected to hydrolysis of proteins at 50° C. for 48 hours; and contents of isoflavone compounds in a soy protein isolate as Embodiment B in which water was added to 200 g of a soy protein isolate in an appropriate amount within a range of 70 to 200 ml and stirring was conducted, and a blend of 50 g of the soy protein isolate in the form of a powder and 0.3 g of koji mold (*Asperillus niger*) was mixed therein, and the thus prepared material was subjected to koji preparation at 30° C. over a period of 48 hours, and water was added to the resulting product in the same weight as that of the resulting product, and the mixture was subjected to hydrolysis of proteins at 50° C. for 48 hours; and contents of isoflavone compounds in a defatted soybean as Comparative Example in which an untreated defatted soybean was subjected to koji preparation at 30° C. over a period of 48 hours in the same manner as in the present invention (Examples) using koji mold (*Aspergillus niger*), and water was added to the resulting product in the same weight as that of the resulting product, and the mixture was subjected to hydrolysis of proteins at 50° C. for 48 hours.

In this manner, organic acids are formed in the initial stage of the fermentation to inhibit contaminants in the soy protein extract and the like from propagating, thereby eliminating undesired possibility of secondary contamination. Consequently, products made from a soy protein extract or the like as a starting material can be mass-produced. Further, even if the water content is not low, it is possible to carry out such treatment for separating glycosidic saccharides from the isoflavone compounds sufficiently.

TABLE 7

(unit: mg/100 g)

|  | Comp. Ex. defatted soybean | Em. A soy protein ext. | Em. B soy protein isolate |
|---|---|---|---|
| daidzin | not detected | not detected | not detected |
| daidzein | 70 | 124 | 67 |
| genistin | 1.3 | 5.5 | 5.4 |
| genistein | 64 | 203 | 133.1 |

(detection limit: 0.5 mg/100 g)

According to Table 7, even in Comparative Example using the untreated defatted soybean as a starting material, daidzein and genistein which are aglycones of isoflavone compounds are contained in greatly increased amounts of 70 mg and 64 mg which are about 21.9 times and 15.2 times as large as those in the untreated defatted soybean shown in Table 1, respectively. As compared with Comparative Example, in Embodiment A of the present invention which uses the soy protein extract as a starting material, daidzein and genistein which are aglycones of isoflavone compounds are contained in further greatly increased amounts of 124 mg and 203 mg which are about 1.8 times and 3.2 times as large as those in Comparative Examples respectively. In Embodiment B of the present invention which uses the soy protein isolate as a starting material, daidzein which is one of the aglycones of isoflavone compounds is contained in an amount of 67 g which is substantially the same amount as that in Comparative Example and genistein which is the other is contained in a further greatly increased amount of 133.1 mg which is about 2.1 times as large as that in Comparative Example.

As described above, according to the present inventions with respect to the isoflavone compounds contained in soybean, the aglycones thereof which have high pharmacological activities can be prepared at extremely high formation ratios.

In particular, in Embodiment A and Embodiment B, genistein which is highly carcinostatic can be prepared at extremely high formation ratios. If a health food to which the thus prepared genistein is added is prepared, a food which is genistein-rich and thus highly carcinostatic can be provided inexpensively because the starting material in each Example is readily available and the genistein is easily prepared.

In the following, description will be given on preparation of a product in which free myo-inositol as a health improving constituent is formed and phytic acid contained in soybean is thereby removed.

In this case, koji mold is propagated on and into the defatted soybean to thereby produce phytase and phosphatase which are enzymes decomposing phytic acid, and by the enzymes, phytic acid contained in the defatted soy bean is hydrolytically removed.

Specifically, from phytic acid which is such a compound that myo-inositol has all of its hydroxyl groups each bonded with a bonded with a phosphoric acid group, the phytic acid-decomposing enzymes liberate the phosphoric acid group(s) to form inositol pentaphosphate, inositol tetraphosphate, inositol triphosphate, inositol diphosphate, inositol monophosphate or inositol alone or a mixture thereof, thereby removing the phytic acid.

As the koji mold used in the koji preparation, there may be employed those which are used in preparation of Japanese traditional fermented foods and tempeh and which are safely used for foods, for example, those having high phytase potency and phosphatase potency and classified as Aspergillus genus such as *Aspergillus usamii, Asperillus kawachii, Aspergillus awamori, Aspergillus saitoi, Aspergillus oryzae* and *Aspergillus niger*; and those classified as Rhizopus genus.

The fermentation time depends upon the type of koji mold used. However, it is at least 24 hours and appropriately selected to be sufficient one for removing phytic acid contained in the defatted soybean to satisfactory extent.

In the subsequent water addition step and hydrolysis step, water is added to the product resulting from the koji preparation, and the mixture is kept in a heated condition at 30 to 55° C. for a predetermined period of time to hydrolyze proteins while sufficiently reducing the amount of phytic acid contained in the defatted soybean by the hydrolytic action of phytase and phosphatase contained in the product.

With respect to the hydrolysis of proteins, hydrolysis time and hydrolysis temperature are appropriately selected depending upon the type of koji mold used so that phytic acid contained in the defatted soybean is sufficiently removed.

The removal of phytic acid is effected by liberating at least one phosphoric acid group from phytic acid which is inositol hexaphosphate. In this connection, the number of the phosphoric acid groups to be liberated may be determined according to intended health promoting activity. In this case, it is preferred to control the number of the phosphoric acid groups to be liberated from phytic acid by adjusting the fermentation time, the hydrolysis time and the hydrolysis temperature depending upon the type, state, properties and amount of the pulse crop, and the type, state, properties and amount of koji mold, and type and properties of the intended product, and so forth.

Table 8 shows a phytic acid content in 100 g of a defatted soybean, with respect to each of an untreated defatted soybean; defatted soybeans A and B which are prepared using two types of shochu koji mold (*Aspergillus niger* and *Aspergillus awamori*), respectively, and each of which is prepared by subjecting a defatted soybean to koji preparation initiated at an initial temperature of 30° C. over a period of 48 hours, adding water to the resulting product in the same weight as that of the resulting product, and subjecting the mixture to hydrolysis of proteins at 30° C. for 24 hours; and a defatted soybean subjected to conventional washing treatment with an alcohol.

TABLE 8

| defatted soybean (d.s.) | phytic acid content (mg/100 g) |
|---|---|
| untreated d.s. | 999 (mg/100 g) |
| shochu koji-treated d.s. A | not detected |
| shochu koji-treated d.s. B | not detected |
| alcohol-washed d.s. | 1150 (mg/100 g) |

(detection limit: 5 mg/100 g)

According to Table 8, in contrast of the phytic acid content of 999 mg (about 1%) in the untreated defatted soybean, in the defatted soybeans A and B each of which is prepared according to the process of the present invention by subjecting an defatted soybean to shochu koji treatment, adding water to the resulting product in the same weight as that of the resulting product, and subjecting the mixture to hydrolysis of proteins at 30° C. for 24 hours, the phytic acid contents are reduced to such levels that no substantial phytic acid is detected, i.e., to such levels that almost all phytic acid is decomposed.

On the other hand, the phytic acid content in the defatted soybean subjected to the conventional washing treatment with an alcohol is 1,150 mg and no reduction of the phytic acid content is observed.

As described above, according to the present invention, phytic acid contained in soybean can be reduced greatly or almost completely.

When the product containing a healthful component thus prepared upon completion of the solid culture treatment is utilized for a food or the like, the product may be used as it is or, as shown in FIG. 1, it may be dried and then pulverized for use as a pulverized product.

Then, description will be given on the product containing a healthful component according to the present invention.

The product of the present invention includes products as such (plain products) which are made from a pulse crop as a starting material, applied products made of the plain product (or containing the plain product as an ingredient), for example, foods, livestock feeds and aquacultural feeds, cosmetics, diets of pets, precursory products for pharmaceutical preparations.

The product made from a pulse crop as a starting material which is prepared in accordance with the process of the present invention may be a food having an extremely low salt content, because it is prepared without being salinized with common salt. Accordingly, the product can be ingested in a sufficient amount when served as a food.

The food contains a healthful component which includes peptides, aglycones of isoflavone compounds, aglycones of saponins, myo-inositol, reaction products resulting from Maillard reaction and so forth. The healthful component is extremely easily absorbed by a digestive tract system of a human being or the like. The healthful component comprises at least one member of the group consisting of liver function improving constituents, cardiac function improving constituents, anti-inflammatory constituents, antifat constituents (flesh reducing constituents), antioxidation constituents and antimutagen constituents, thereby enabling dietarily desired life to be realized which exhibits excellent effect in terms of health maintenance of a human being.

For example, when the food comprising the product of the present invention is formed into a form convenient for eating, such as biscuit, cookie or the like, it is possible to ingest the healthful component which is excellent in liver function improving activity, cardial function improving activity, anti-inflammatory activity, antifat (flesh reducing) activity, antioxidation activity, antimutagen activity and the like while eating such an article as a food. In particular, by simply eating such biscuit or the like in an amount covering the intake of the healthful component per day which is required to attain the above-mentioned health improving activities, the biscuit or the like contributes to prevention of attack of the disorders.

When the product in accordance with the above-described procedure is utilized as a feed or the like, as shown in FIG. 1, the defatted soybean prepared as in the above-described embodiments is dried and then pulverized to obtain a product as a pulverized defatted soybean having high pharmacological activities, such as material for a livestock feeds an aquacultural feed or the like.

According to the process of the present invention, formation of aglycones of isoflavone compounds and aglycones of saponins, which have high pharmacological activities, at extremely high formation ratios; removal of phytic acid in the pulse crop; and hydrolysis of proteins are effected by propagating living koji mold. Therefore, the formation of aglycones and the removal of phytic acid can be effected with ease even in a pulse crop in solid state. Accordingly, simplified preparation procedure and reduced preparation cost are realized.

Further, the preparation process of the present invention can be carried out using a conventional koji preparation device without any alteration, and hence it is not required to specially manufacture a basic production device, thereby providing wide utilities.

The health promoting activities according to the product of the present invention will be described with reference to specific Examples.

EXAMPLE 1

In this Example, with respect to liver function improving activity, comparison on metabolic decomposition rate of acetaldehyde was made between a feed containing an unfermented defatted soybean as an ingredient and a feed containing a fermented defatted soybean prepared according to the process of the present invention as an ingredient.

Method of Test

Each of the an unfermented defatted soybean-containing feed and the fermented defatted soybean-containing feed prepared according to the present inventions which are prescribed in Table 9, was fed to 15 ddy male mice of about 20 g in body weight for 4 weeks, and then a 5% suspension of acetaldehyde (suspended in distilled water) was intracelially administered in an amount of 10 ml per kg in a body weight to cause coma. Individually, the coma time from then to recovery from the coma was measured.

TABLE 9

| | Test Feeds | |
|---|---|---|
| | unfermented d.s.-cont. feed (g/kg) | fermented d.s.-cont. feed (g/kg) |
| unfermented d.s. | 402 | — |
| fermented d.s. | — | 359 |
| corn oil | 50 | 50 |
| vitamin mixture (pre-mix) | 10 | 10 |
| mineral mixture (pre-mix) | 35 | 35 |
| cellulose | 12 | — |
| α-corn starch | 291 | 346 |
| sucrose | 200 | 200 |

(d.s.: defatted soybean)

As shown in the following Table 10 the results of the measurement shows that the coma time of the group fed with the unfermented defatted soybean-containing feed is as long as about 96 minutes whereas the coma time of the group fed with the fermented defatted soybean-containing feed prepared by the process of the present invention is about 71 minutes and shorter than that of the former group by about 25 minutes. Accordingly, the product of the present invention is capable of accelerating metabolic decomposition of acetaldehyde and thus capable of preventing hangover, nasty aftereffects of drinks and the likes and capable of improving liver function.

TABLE 10

Influence of Administration of Acetaldehyde on Coma Time

|  | coma time (min.) |
|---|---|
| unfermented d.s.-cont. feed (n = 15) | 96 ± 9[a] |
| fermented d.s.-cont. feed (n = 15) | 71 ± 7[b] |

(d.s.: defatted soybean)

EXAMPLE 2

Based on the fact that the fermented defatted soybean was found to have effect of reducing time of coma induced by acetaldehyde in Example 1, comparison was made in this Example on influence of a protein source on acute toxicity of acetaldehyde among various protein sources including the fermented defatted soybean prepared by the process of the present invention.

Method of Test

Each of an unfermented defatted soybean, the fermented defatted soybean prepared by the process of the present invention, casein, egg white and gluten, which are shown in the following Table 11, was fed to 14 ddy male mice of about 20 g in body weight for 4 weeks, and then a 10% suspension of acetaldehyde (suspended in distilled water) was intracelially administered in an amount of 10 ml per kg in a body weight. With respect to each of the groups, survival rate was measured.

TABLE 11

| | protein source in feed (survival rate) | | | | |
|---|---|---|---|---|---|
| | fermented d.s. | unfermented d.s. | casein | egg white | gluten |
| the day of adm. | 11/14 (79%) | 10/14 (71%) | 8/14 (57%) | 5/14 (36%) | 2/14 (14%) |
| 1 day later | 11/14 (79%) | 9/14 (64%) | 8/14 (57%) | 5/14 (36%) | 0/14 (0%) |
| 2 days later | 8/14 (57%) | 6/14 (43%) | 7/14 (50%) | 4/14 (29%) | 0/14 (0%) |
| 3 days later | 8/14 (57%) | 4/14 (29%) | 7/14 (50%) | 3/14 (21%) | 0/14 (0%) |
| 4 days later | 6/14 (43%) | 3/14 (21%) | 5/14 (36%) | 3/14 (21%) | 0/14 (0%) |
| 5 days later | 6/14 (43%) | 3/14 (21%) | 4/14 (29%) | 3/14 (21%) | 0/14 (0%) |

From the results of the measurement, it was confirmed that the group of the mice fed with the feed containing the fermented defatted soybean prepared by the process of the present invention as a protein source showed a survival rate higher than any of those of the groups of mice respectively fed with the unfermented defatted soybean-containing feed, casein, egg white and gluten as protein sources, and that by feeding the feed containing the fermented defatted soybean prepared by the process of the present invention, the group of mice fed therewith had improved acetaldehyde decomposing capability. In other words, it is considered that the fermented defatted soybean-containing feed had an effect of increasing activity of aldehyde dehydrogenase which is phase II xenobiotic-metabolizing enzymes to enhance carcinogen detoxication and elimination. The function is considered to be attributable to the activities of the product prepared by subjecting a defatted soybean to koji preparation by means of koji mold, followed by hydrolysis to enzymatically cause changes in components of soybean.

EXAMPLE 3

In this Example, evaluation on antioxidation activities was made using products prepared by the process of the present invention and other materials as specimens in accordance with AOM test. The results are shown in FIG. 3.

The products according to the present invention used as the specimens were a fermented soy protein extract exracted with ethanol: 0.1% and a fermented soy protein extract extracted with ethanol: 0.5%. As the other specimens, an untreated soy protein extract (plain product), an untreated soy protein extract extracted with ethanol: 0.1%, koji mold extracted with ethanol: 0.1%, and 98% α-tocopherol: 0.1% were employed.

In AOM (Active Oxygen Method) tests each of the specimens is added to lard, and the mixture is heated at a temperature of 90° C. to measure a peroxide value (POV) with time.

Figure 3:
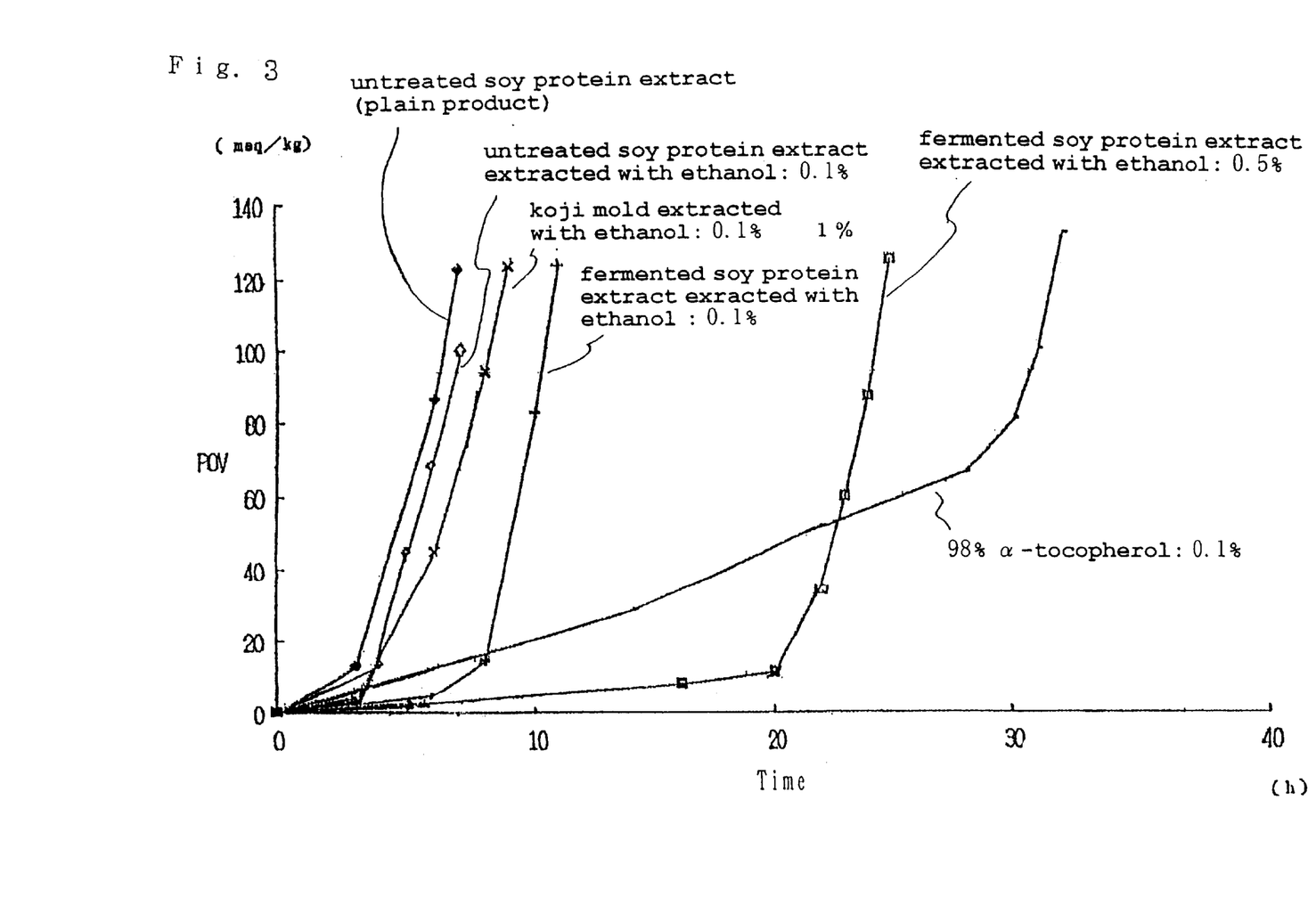
FIG. 3 is a graphical representation showing characteristics of specimens according to AOM (Active Oxygen Method) test where the products prepared by the process of the present invention and other materials were used as the specimens.

From the results in FIG. 3, it is understood that the fermented soy protein extract exracted with ethanol: 0.1% and the fermented soy protein extract extracted with ethanol: 0.5% as the products according to the present invention showed prolonged periods of time before increases in peroxide values (POV) and thus have superior antioxidation activities as compared with the untreated soy protein extract.

Accordingly, in common with α-tocopherol, the product of the present invention has antioxidation activity. If the product is incorporated in a greasy dish in a small amount, peroxidation of oil is prevented. It is thereby possible to prevent hepatopathy attributable to lipoperoxide.

EXAMPLE 4

In this Example, in relation to antimutagen activity, each of whole soybean and a defatted soybean as two starting materials was subjected to the process of the present invention to prepare an intermediate product which was hot air-dried posterior to koji preparation (post-koji preparation product) and a product which was hot air-dried posterior to hydrolysis (post-hydrolysis product). The percent suppression of the every products on the SOS responese of *Salmonella typhimurium* induced by MNNG (N-methyl-N'-nitrosoguanidine) was determined.

TABLE 12

|  |  | Suppresion (MNNG, %) |
|---|---|---|
| whole soybean | untreated material | 22.5 |
|  | post-koji preparation product (hot air-dried product) | 15.2 |
|  | post-hydrolysis product (hot air-dried product) | 60.2 |
| defatted soybean | untreated material | 0.8 |
|  | post-koji preparation product (hot air-dried product) | 24.5 |
|  | post-hydrolysis product (hot air-dried product) | 34.7 |

The results are as shown in the above Table 12 and show that the rates of inhibition tend to be maximized posterior to the hydrolyses. Based on this, it is considered that reaction products resulting from Maillard reaction are formed by the hydrolyses. As described above, in the present invention, Maillard reaction products are formed as in a miso. Further, the present invention has an effect that since no common salt is added as opposed to a miso or soy sauce, the time of the hydrolysis subsequent to the koji preparation can considerably be shortened.

It is to be understood that the present invention is by no means restricted to the above-described embodiments and Examples and that various alteration and modification may be made according to need.

I claim:

1. A process for producing health-promoting products comprising the ordered steps of:
   (a) preparing a starting material from legumes;
   (b) inoculating koji mold on said starting material for at least 24 hours;
   (c) adding water to the resultant from said staring material and koji mold;
   (d) hydrolyzing said resultant for in water for at least 24 hours; and
   (e) extracting a health promoting product having at least one healthful components selected from the group consisting of liver function-improving constituents, cardiac function-improving constituents, fat-reducing constituents, anti-oxidation and anti-inflammatory constituents.

2. A process for producing health promoting products according to claim 1, wherein the step of preparing a starting material includes cooking and cooling.

3. A process for producing health promoting products according to claim 1, wherein said legumes are selected from the group consisting of soybean, defatted soybean, soy protein extract, and soy protein isolate.

4. A process for producing health promoting products according claim 2, wherein proteins, glycosidic isoflavone compounds, soyasaponins, and phytic acid are respectively converted into peptides, aglycones of the glycosidic isoflavone compounds, aglycones of the soyasapoins, and myo-inositol or compounds resulting from Maillard reaction.

5. A process for producing health promoting products according to claim 4, wherein said legumes substantially comprises defatted soybean.

6. A process for producing health promoting product according to claim 4, wherein said step of inoculating koji mold is carried out at between 28° C. and 40° C., and said step of adding water is carried out at between 30° C. and 65° C.

7. A health promoting product containing at least one compound selected from the group consisting of aglycones of glycosidic isoflavone compounds, aglycones of soyasapoins and myo-inositol prepared by the steps of preparing a starting material of legumes, inoculating koji mold on said starting material, adding water to said starting material and koji mold, hydrolyzing said starting material in water and extracting a health promoting product having at least one healthful component selected from the group consisting of liver function improving constituents, cardiac function-improving constituents, anti-inflammatory constituents, fat-reducing constituents and anti-oxidation constituents.

8. A health promoting product according to claim 6, wherein said step of inoculating koji mold is carried out at between 28° C. and 40° C. for at least 24 hours, and said step of adding water is carried out at between 30° C. and 65° C., and said step of hydrolyzing said resultant lasts for at least 24 hours.

* * * * *